United States Patent [19]

LeVeen et al.

[11] Patent Number: 5,388,449
[45] Date of Patent: Feb. 14, 1995

[54] OSMOLARITY SENSOR

[76] Inventors: Harry H. LeVeen, 321 Confederate Cir.; Eric G. LeVeen, 19 Palmetto Rd., both of Charleston, S.C. 29407; Robert F. LeVeen, 815 S. 94th St., Omaha, Nebr. 68114

[21] Appl. No.: 88,228

[22] Filed: Jul. 6, 1993

[51] Int. Cl.[6] .................. G01N 13/04; G01N 7/10
[52] U.S. Cl. .................. 73/64.47; 422/82.02; 422/82.09
[58] Field of Search ............... 422/82.01, 82.05, 422/82.09, 99, 101; 436/108, 148, 150, 149, 178; 73/64.47

[56] References Cited

U.S. PATENT DOCUMENTS

| Re. 31,879 | 5/1985 | Lubbers et al. | 436/133 |
|---|---|---|---|
| 3,635,075 | 1/1972 | Gilbert | 73/64.47 |
| 4,015,462 | 4/1977 | Greyson et al. | 73/64.47 X |
| 4,028,931 | 6/1977 | Bisera et al. | 73/64.47 |
| 4,455,864 | 6/1984 | Wallner | 73/64.47 |
| 4,475,556 | 10/1984 | Reiff | 73/64.47 X |
| 4,538,616 | 9/1985 | Rogoff | 128/632 |
| 4,592,973 | 6/1986 | Pemsler et al. | 429/206 |
| 4,671,331 | 6/1987 | Pruden | 141/98 |
| 4,706,495 | 11/1987 | Steudle et al. | 73/64.47 |
| 4,784,811 | 11/1988 | Hirschfeld | 264/1.4 |
| 4,802,982 | 2/1989 | Lien | 210/247 |
| 4,832,009 | 5/1989 | Dillon | 602/58 |
| 4,869,821 | 9/1989 | Korin | 210/321.64 |
| 5,005,403 | 4/1991 | Steudle et al. | 73/64.47 X |
| 5,028,337 | 7/1991 | Linder et al. | 210/642 |
| 5,066,683 | 11/1991 | Dillon et al. | 523/466 |
| 5,132,298 | 7/1992 | Ueno | 514/58 |
| 5,141,873 | 8/1992 | Steudle et al. | 73/64.47 X |
| 5,173,225 | 12/1992 | Range et al. | 264/45.5 |
| 5,176,953 | 1/1993 | Jacoby et al. | 428/315.5 |

FOREIGN PATENT DOCUMENTS 2640378 6/1990 France.
2353659 4/1975 Germany.

OTHER PUBLICATIONS

Steele et al. "A New High Speed Membrane Osmometer" Pittsburgh Conference on Analytical Chem. and Applied Spectroscopy, 1963.

Primary Examiner—Robert J. Warden
Assistant Examiner—Robert Carpenter
Attorney, Agent, or Firm—Herbert F. Ruschmann

[57] ABSTRACT

An osmolarity sensor continuously senses an osmolarity of a fluid. A principle of operation is based on achieving an equilibrium of a vapor pressure of a specimen solution with a vapor pressure of a standard solution. In an embodiment, the standard solution is contained in a cavity defined by a vapor-permeable membrane which is immersed in a specimen solution. The standard solution and the specimen solution are allowed to come into equilibrium by a movement of water vapor across the vapor-permeable membrane, which is permeable only to water vapor and not to any solutes or water itself. The movement of the water vapor between the standard solution and the specimen is measured by sensing a volume of water transferred between the standard solution and the specimen solution. A measurement of a volume change of the standard solution is made by sensing a change a conductivity of the standard solution. Alternatively, the volume change is determined by measuring a change in a photo-absorbance of the standard solution with a chromophore added therein. In yet another embodiment the volume change is determined by a direct visual measurement of the volume of the standard solution.

26 Claims, 5 Drawing Sheets

OSMOLARITY SENSOR

BACKGROUND OF THE INVENTION

The present invention relates to a sensor for detecting an osmolarity of a specimen solution, and more particularly, to a sensor having a standard solution separated from the specimen solution by a membrane permeable to a vapor of a solvent and neither the solvent itself nor the solutes therein. The present invention is suitable for applications involving measurement of an osmolarity of a solution, including measuring an osmolarity of urine for the purpose of determining a level of kidney function.

An understanding of osmosis is necessary for the comprehension of the present invention and is therefore briefly reviewed. If two aqueous solutions of identical composition, but different concentrations, are separated from one another by a membrane permeable to water, but not to dissolved solutes of the solution, the water is transferred across the membrane to a side of denser concentration. At equilibrium, sufficient water is transferred so that the concentration of the solute on both sides of the membrane is identical. This passage of water in the direction of greater solute concentration is called osmosis.

The tendency of a solvent to pass through a semipermeable membrane is characterized by an osmotic pressure of the solution. For example, if a volume of fluid on the denser side of the solutions is in a contained space and not free to expand, because its capacity was limited by rigid walls, a pressure is developed in the contained space. An amount of pressure required to prevent an entry of water is called the osmotic pressure.

It is not strictly correct to refer to an osmotic pressure as being exerted by solutes, for example glucose, plasma proteins, or electrolytes, since solutes do no act by exerting a negative pressure across the membrane. Instead, it is a property of water which exerts a vapor pressure at any given barometric pressure and temperature. In that respect, water follows the gas laws. A boiling point of an aqueous solution is raised by solutes and a freezing point is depressed. This information serves as the basis for apparati used to measure the osmotic pressure of solutions.

If an aqueous solution is separated from pure water by a membrane, a potential pressure difference between the two phases is created and equilibrium is achievable by three mechanisms. In a first mechanism, an equal concentration of solute on both sides of the membrane may be established where the membrane is permeable to the diffusible solute. In a second mechanism, where the solute is not diffusible, water passes through the membrane thereby diluting the solution by osmosis and allowing a change in pressure and concentration on the respective sides to achieve an equilibrium of the system. Finally, a third mechanism utilizes an application of external pressure upon a solution, to oppose the osmotic pressure of the water, creating an opposing hydrostatic pressure preventing the movement of the water.

Osmolar Concentration

Osmotic pressure of a solution is a colligative property and therefore depends solely on a number of particles in an aqueous solution in the form of undissociated molecules (such as glucose), ions (such as $Na^+$ or $Cl^-$), colloidal micelles (such a proteins and some colloids); and not on their size or weight. The gram molecular weight of any undissociated substance dissolved in a liter of water would exert an osmotic pressure of 22.4 atmospheres under ideal conditions with an ideal membrane. Therefore, when discussing osmotic pressure, it is the molar concentration of a solution which is of significance. For example, a molar solution of glucose (molecular wight=180), which does not dissociate, would exert an osmotic pressure of 22.4 atmospheres. However, a molar solution of sodium chloride would exert an osmotic pressure of almost twice that amount since it almost completely dissociates into $Na^+$ and $Cl^-$ ions. Thus, a glucose solution of 100 mg/dL (1 Gm/L), as in human plasma, has an osmotic pressure of 22.4/180 atmospheres (95 mm Hg).

Because osmotic pressure is dependent on a concentration of osmotically significant particles, osmolarity is best expressed as osmols per liter, where an osmol corresponds to a mole of such particles. (1,000 milliosmols=1 osmol).

Gibbs-Donnan Membrane Equilibrium

The Gibbs-Donnan Membrane Equilibrium describes the condition of a system at equilibrium wherein two solutions are separated by a semipermeable membrane and both contain common diffusible ions while one contains a non-diffusible ion. Consider two ionized solutions, A and B occupying compartments of fixed volumes which are separated by a semipermeable membrane. At equilibrium the following conditions exist: (1) each solution contains the same number of anions as cations, i.e. they will be electrically neutral; and (2) a product of the diffusible ions on one side of the membrane will equal a product of the diffusible ions on the other side of the membrane. However, if one or more non-diffusible ions are also present, the ionic distribution of the diffusible ions will be asymmetrical at equilibrium. For instance, if one side contained $Na+$, $Cl^-$ which were diffusible and an $X^-$ ion which was non-diffusible, and the other side of the membrane contained only the diffusible ions $Na^+$ and $Cl^-$, at equilibrium the $Na^+$ concentration on the side of the membrane containing the non-diffusible ion would be greater that on the side where both of the ions were diffusible and the $Cl^-$ ion will be greater than on the side containing the non-diffusible ion. Thus, this fact, known as Gibbs-Donnan Membrane Equilibrium, results in an unequal distribution of diffusible ions across a membrane.

Therefore, if diffusible and non-diffusible substances are present, only the non-diffusible ones will contribute permanently to a pressure increment since the other solutes will be equally distributed at equilibrium.

Active Transport

In the previous discussion, we assumed that the walls of the container were rigid, as in many vegetable cells, but in animal cells the walls are non-rigid and water can move from one side of the membrane to the other. With no limitation on volumes, water would pass into the cell as long as an intracellular osmotic pressure is greater than an osmotic pressure of the surrounding aqueous medium. The passage of fluid to the intracellular position would cause the cell to swell and it would continue to swell until the extracellular osmotic pressure was the same as the intracellular osmotic pressure. If equilibration of the osmotic pressure was not established, the cell would continue to swell until it ruptured. To prevent this from happening, and to keep cells at a constant volume, active transport occurs.

Active transport in a cell is adjusted to oppose the Donnan effect and to maintain a stable cellular osmolarity and volume. The result is that an excess of cation, or water, does not accumulate in the cell. Even large differences of tonicity across normal cell membranes does not cause large hydrostatic pressures to develop. Because the system is not in true ionic equilibrium, considerable amount of metabolic work must be performed to maintain this state against an unequal gradient. The work performed continuously to maintain or increase concentration difference across a membrane is called osmotic work.

The kidneys do osmotic work in concentrating solutes in the urine greater than they exist in the plasma. Concentrating a urea solution from 0.03 percent as occurs in plasma to 2%, as occurs in the urine, requires 2.5 kilocalories per mole regardless of whether this concentration results from a direct transfer of water or a transfer secondary to the movement of $Na^+$.

The measurement of the osmolarity of urine is of extreme physiologic importance, since the ability of the kidney to do osmotic work is the first function to be lost in renal damage. A change in the daily or hourly urinary osmolarity would therefore be the earliest indication of renal damage. The urine would become isosmotic with the plasma and its urea concentration would fall and become identical to that of plasma. For this reason, a method for the determination of urinary and plasma osmolarity is of great clinical significance.

The only sensitive method for determining the osmolarity of such solutions now in clinical use depends on the determination of the vapor pressure of water at its dew point. Determination of a lowering of a freezing point of an aqueous sample is a less sensitive method and is therefore not used. At the present time, the measurement of osmolarity can only be performed in a laboratory and requires expensive equipment and a skilled technician to operate it. The laboratory test is further burdened by expenses entailed in its measurement and the length of time lost in the interval from the collection of the sample to the availability of the information to the physician. Since there is no available sensor for the measurement of osmolarity, repeated osmolarity measurements at short intervals is usually not possible and is prohibitively expensive.

SUMMARY OF THE INVENTION

Accordingly, it is an object of the invention to provide a sensor for detecting an osmolarity of a solution which overcomes the drawbacks of the prior art.

It is a further object of the invention to provide a sensor for detecting osmolarity which permits an osmolarity measurement to be made in an expeditious and reliable manner.

It is a still further object of the invention to provide an osmolarity sensor which permits osmolarity measurements to be made without the need for expensive laboratory equipment requiring highly skilled technicians for its operation.

Yet another object of the present invention is to provide an osmolarity sensor which permits an individual to perform an osmolarity measurement outside of a laboratory and in a real-time fashion. For instance, the measurement may be made at the location where the measurement is needed, such as a patient's hospital room, so that a course of action may be taken based a measurement that accurately reflects a current condition.

Briefly stated, there is provided an osmolarity sensor which is used to continuously measure and indicate the osmolarity of any specimen solution, A standard solution is separated from a specimen solution by a membrane permeable only to a water vapor, and not to any solutes or the solvent; in the case of the present example, water itself. The method of operation is based on an equilibrium of the vapor pressure of the specimen solution with respect to the vapor pressure of the standard solution. The standard solution and the specimen solution are allowed to come into equilibrium by a movement of water vapor across the vapor-permeable membrane. The movement of water vapor across the vapor-permeable membrane, between the standard solution and the specimen, is measured by sensing a volume of water transferred to or from the standard solution. A measurement of a volume change of the standard solution is made by sensing a change in a conductivity of the standard solution, a change in an absorbance of the standard solution including a chromophore, or by a direct visual measurement of a change in the volume of the standard solution. Thus, the osmolarity of the specimen may be determined by determining the volume change of the standard solution since this is indicative of the specimen's osmolarity. Features of the present invention include two vapor-permeable membranes, permeable to gases, that are compressed between two rigid, semirigid or flexible rings. The vapor-permeable membranes are loosely suspended between the two rings. The membranes are sealed at their edges by a silicone 0-ring. An expandable closed cavity is thus created between the two vapor-permeable membranes into which the standard solution is introduced. Once charged with the standard solution the sensor is introduced into a specimen solution.

Another feature of the present invention includes the standard solution being an electrolyte solution containing 200 milliosmols per liter which is less than the osmolarity of plasma, which is 310 milliosmols per liter. Therefore, if the specimen solution is isosmotic with blood it will draw water vapor from the standard solution until its osmolarity corresponds to that of plasma. A volume of the standard solution is thus decreased and an osmolarity of the specimen solution is determined accordingly. Given that the standard solution has a known osmolarity before reaching equilibrium with the specimen solution, the osmolarity of the specimen solution may be determined from the change in volume of the standard solution and its corresponding change in concentration.

Yet another feature of the present invention includes a response time required for the vapor pressure of the standard solution to reach equilibrium with that of the specimen solution which permits timely measurement of osmolarity of the specimen solution. The response is dependent on a ratio between a volume of the standard solution and a surface area of the vapor-permeable membranes. The smaller the volume of the standard solution the shorter will be the response time, provided a surface area of the vapor-permeable membranes is constant. Also, the greater the surface area of the vapor-permeable membranes, for any fixed volume of standard solution, the shorter the response time will be. The surface area of the vapor-permeable membrane and the volume of the standard solution is adjusted such that timely measurements are achieved.

Still other features of the present invention include sensors for determining the volume of the standard solution. A small conductivity cell may be suspended in the standard solution so that a measurement of concentration or dilution of the standard solution, indicative of a volume change, may be obtained based upon a change in the conductivity of the standard solution. A concentration of electrolytes is directly proportional to the conductivity of a solution. An osmolarity of any electrolyte solution has a known relationship to its concentration. Thus, measurement of the concentration of the standard solution is easily determined by measuring its conductivity, and it follows that the volume of the standard solution and the osmolarity of the specimen solution may therefore be found. Furthermore, the small conductivity cell permits the osmolarity of the specimen solution, related to the conductivity of the standard solution, to be continuously sensed. Alternatively, a fiber-optic sensor is introduced into a standard solution containing a chromophore to detect volume changes where the standard solution is contained between flexible walls.

A further feature of the present invention employs vapor-permeable membrane materials, for use with aqueous solutions, which are available and, for the most part, are strongly non-polar (hydrophobic) and have microporous communications, from one side of the membrane material to the other side, comprising minute canaliculi. Water has a high surface tension and therefore does not penetrate the minute canaliculi. Solutes are unable to pass without the aqueous liquid in which they are dissolved. Nonetheless, water vapor and gases freely pass through the canalicular channels.

In a slightly different configuration the specimen solution flows around the sensor, in contact with the vapor-permeable membranes and contained within a flow-through housing.

The present invention provides an osmolarity sensor, employing a an aqueous solution of electrolytes as a standard solution, for measuring an osmolarity of a specimen solution, comprising: means for containing the standard solution defining a cavity wherein the standard solution is held; the means for containing including a vapor-permeable membrane separating the standard solution from the specimen solution; the vapor-permeable membrane permitting passage of a solvent of the specimen solution and the standard solution and blocking passage of solutes of the specimen solution and means for sensing a volume of the standard solution, so that the osmolarity of the specimen solution is determinable when the standard solution has achieved substantial osmotic equilibrium with the specimen solution at substantially equal hydrostatic pressures.

Furthefore, the present invention provides an osmolarity sensor, employing a standard solution for measuring an osmolarity of a specimen solution into which the osmolarity sensor is immersed, comprising: means for containing the standard solution defining a cavity wherein the standard solution is held; the means for containing including a vapor-permeable membrane separating the standard solution from the specimen solution; the vapor-permeable membrane permitting passage of a solvent of the specimen solution and the standard solution and blocking passage of solutes of the specimen solution; and means for sensing a concentration of the standard solution, disposed within the cavity so that the osmolarity of the specimen solution is determinable when the standard solution has achieved substantial osmotic equilibrium with the specimen solution at substantially equal hydrostatic pressures.

These and other objects, features and advantages of the present invention will become apparent from the following description read in conjunction with the accompanying drawings, in which like reference numerals designate the same elements.

BRIEF DESCRIPTION OF THE DRAWINGS

FIG. 2b shows a longitudinal cross-sectional view of the embodiment of FIG. 1, taken along line IIb—IIb of FIG. 2a.

DETAILED DESCRIPTION OF PREFERRED EMBODIMENTS

Figure 1:
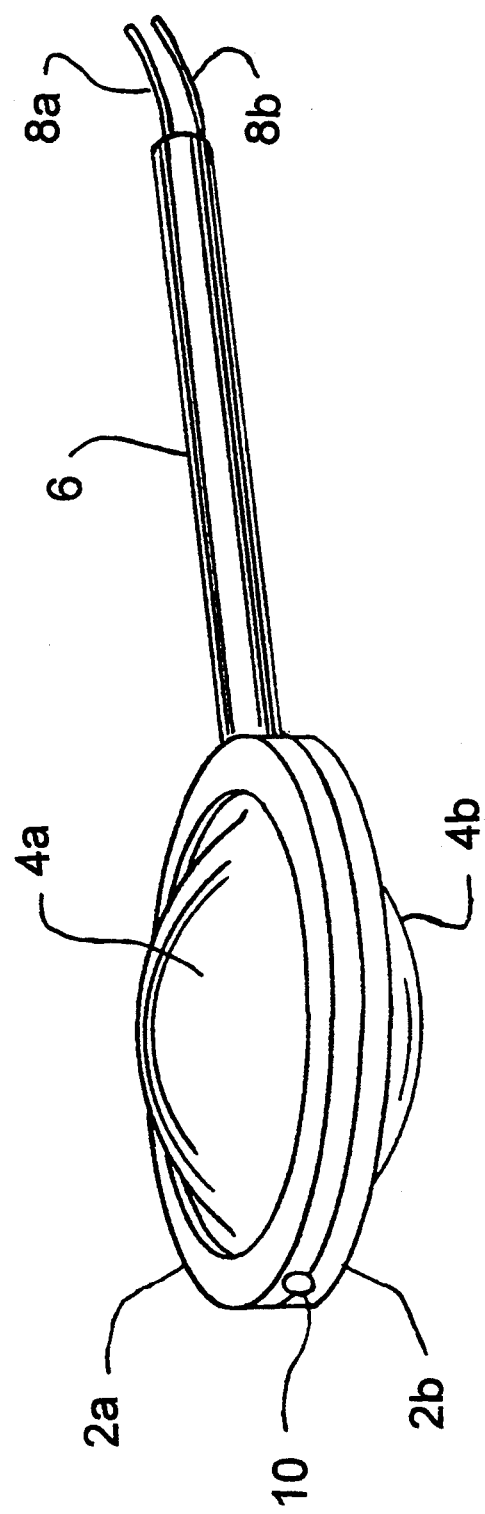
FIG. 1 shows a perspective view of a first embodiment of the invention in a dip-type sensor configuration.

Referring to FIG. 1, an embodiment of a dip-type sensor 1 of the present invention is shown. The sensor includes first and second circular non-polar plastic rings, 2a and 2b, which are fused together and may be formed from various plastics including polyolefin. The plastic rings, 2a and 2b, and compress two non-polar vapor-permeable membranes, 4a and 4b, and an O-ring (not shown) therebetween. The membranes, 4a and 4b, have a characteristic of transmitting only gases and no aqueous liquids. A handle 6 is affixed to the plastic rings, 2a and 2b. Two sensor leads, 8a and 8b, emerge from an end of the handle 6 and are connected to a metering device (not shown). A nipple 10, formed of a silicone rubber and integral with the O-ring, is also compressed between the plastic rings, 2a and 2b, and extends into a cavity between the membranes, 4a and 4b. The nipple 10 allows a user to inject a standard electrolyte solution (not shown) into the cavity by means of a syringe needle (not shown) expanding the membranes, 4a and 4b, to a shape as generally shown. The membranes, 4a and 4b, have sufficient slack so as not to exert pressure upon the standard solution. Once the needle is withdrawn from the nipple 10, the nipple 10 seals itself. The dip-type sensor 1 is then immersed in a specimen liquid.

It is realized that alternative embodiments of the present invention may employ a tubular inlet for the purpose of introducing the standard solution into the cavity 13 wherein the tubular inlet is sealed after charging is completed. Alternatively, a silicone button may be fused directly to one of the first and second membranes, 4a and 4b, so that a needle may be used to charge the cavity 13 and then removed, after which the silicone seals itself. These and other embodiments realizable by those skilled in the art in view of this disclosure are within the scope and spirit of the present invention.

Figure 2A:
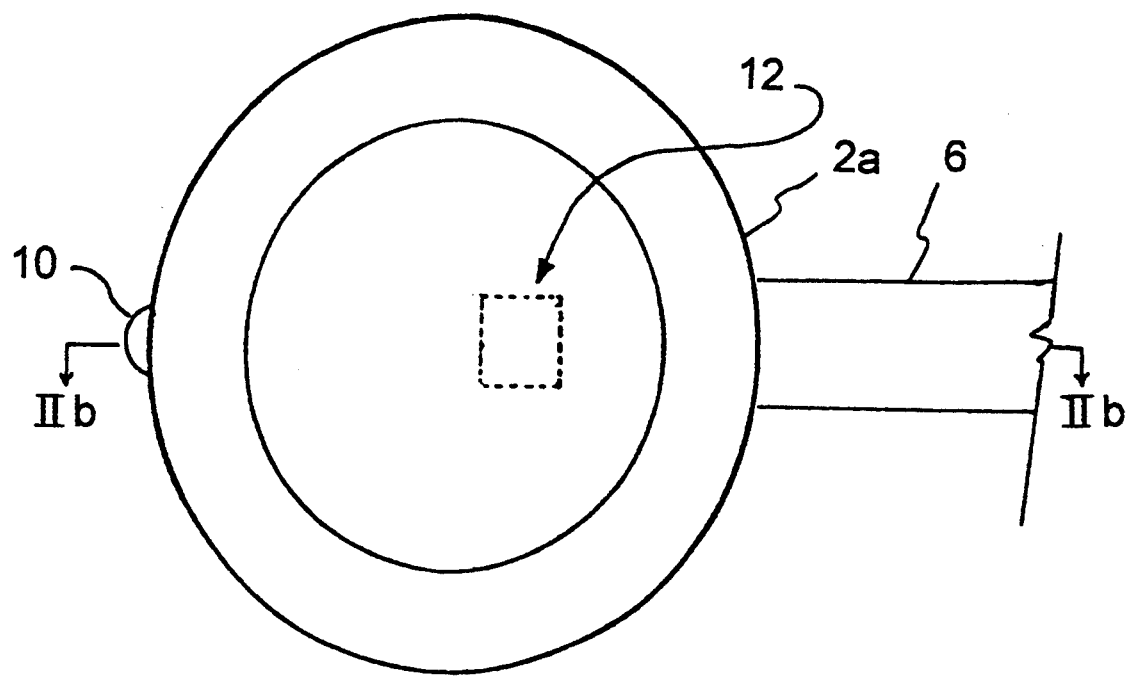
FIG. 2a shows a top plan view of the embodiment of FIG. 1 indicating a location of a conductivity sensor.
Figure 2B:
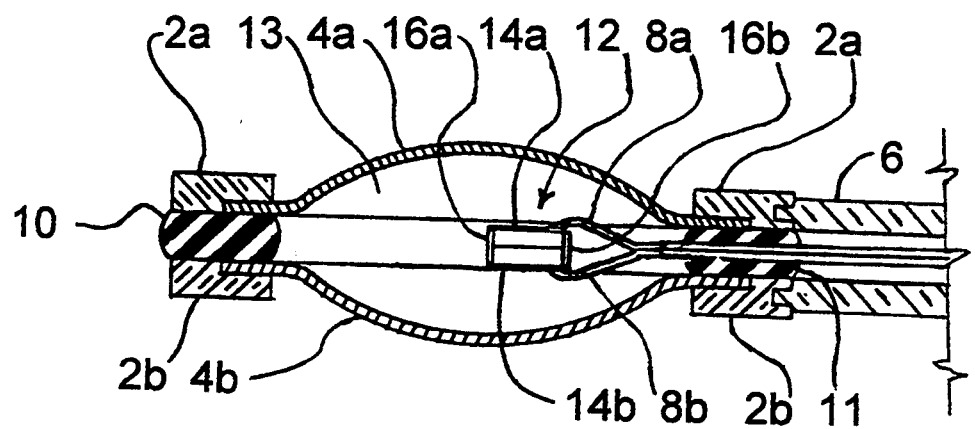

Referring to FIGS. 2a and 2b, the dip-type sensor 1 has a conductivity sensor 12 suspended within the cavity 13. The conductivity sensor 12 is of conventional design having a first and a second conductive plate, 14a and 14b, separated by non-conducting standoffs, 16a and 16b. The sensor leads, 8a and 8b, connect to the first and second conductive plates, 14a and 14b, and extend externally through a sealing gland 11 which is also integral with the O-ring (not shown). The conductivity sensor 12 senses a conductivity of the standard electrolyte solution (not depicted) within the cavity 13 and is monitored by conventional conductance measuring equipment, such as an ohmmeter or a Wheatstone bridge device, via the sensor leads, 8a and 8b.

In the present embodiment, the membranes, 4a and 4b, are permeable to water vapor but not to water or solutes in the standard solution or the specimen solution. The dip-type sensor 1 is submersed in the specimen solution and water vapor is transferred from sides of the membranes, 4a and 4b, where a higher vapor pressure (lower osmotic pressure) exists to sides where a lower vapor pressure (higher osmotic pressure) exists. Therefore, if the standard solution has a higher vapor pressure than does the specimen solution, the water vapor will be transferred to the sides where the specimen solution is. The transfer is reversed where the relationship of vapor pressures is reversed. The spaces on both of the sides of the membranes, 4a and 4b are not restricted so water vapor will transfer until equilibrium is reached at which time the water vapor pressures are substantially identical. Water vapor transferred to the side with low vapor pressure will immediately be condensed to liquid thus lowering the concentration of the solution on the denser side. Consequently, a standard solution volume will decrease.

The conductivity sensor 12 permits measurement of the standard solution volume. Since equilibrium is achieved by the transfer of water vapor either into or out of the cavity 13, the concentration of the standard solution will vary accordingly. As the concentration of electrolytes vary so does the conductivity. Identity of solutes of the standard solution, which are in the present example electrolytes, remains constant since only water vapor is transferred, and thus provides a constant in the calculation of concentration based on conductivity. Similarly, a quantity of such solutes remains constant which permits calculation of the volume of the standard solution. Thus, since a change in concentration of the standard solution is related to its volume, the osmolarity of the specimen solution may readily be determined from a conductivity measurement of the standard solution. The mathematical relationships between the conductivity of the standard solution, the volume change, the resultant vapor pressure of the standard solution, and the osmolarity of the specimen solution having an equivalent vapor pressure, may be readily determined by those skilled in the art in view of this disclosure.

Figure 3A:
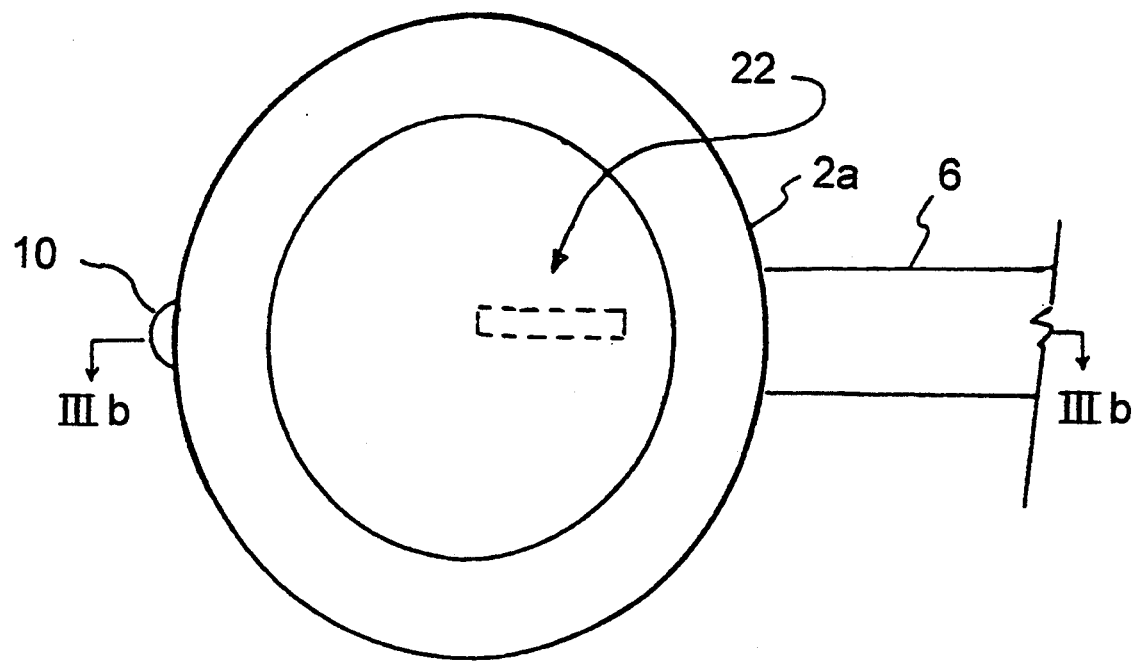
FIG. 3a shows a top plan view of another embodiment of the present invention in a dip-type configuration employing an optical sensor.
Figure 3B:
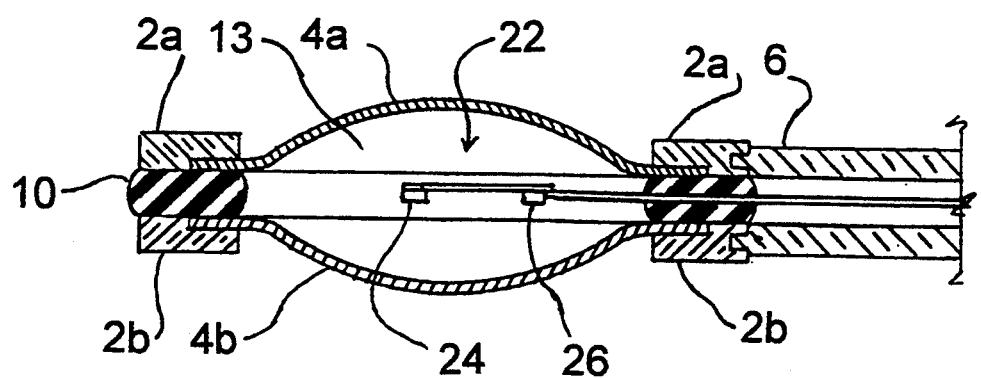
FIG. 3b shows a longitudinal cross-sectional view of the embodiment of FIG. 3a taken along line IIIb—IIIb.

Referring to FIGS. 3a and 3b, a second embodiment of the present invention provides a dip-type sensor 20 similar to the above embodiment except as stated herein. The cavity 13 has a standard solution (not depicted) with a chromophore introduced therein and an optical sensor 22 suspended in the standard solution. The optical sensor 22 measures an absorbance of the standard solution at a wavelength suited to the chromophore. The concentration of the standard solution may then be readily determined from the absorbance by application of Beer's Law. The optical sensor 22 is of conventional design and includes a light emitting diode (LED) 24 spaced apart from a photosensitive cell 26. The LED 24 is driven by an appropriate supply (not shown) and an output of the photosensitive cell is appropriately sense.

It is realized that an optical fiber could be introduced into the cavity 13 in place of the photosensitive cell 26 so that light emitted by the LED 24 could be sensed externally. Similarly, another optical fiber could be used to introduce light in place of the LED 24.

Figure 4A:
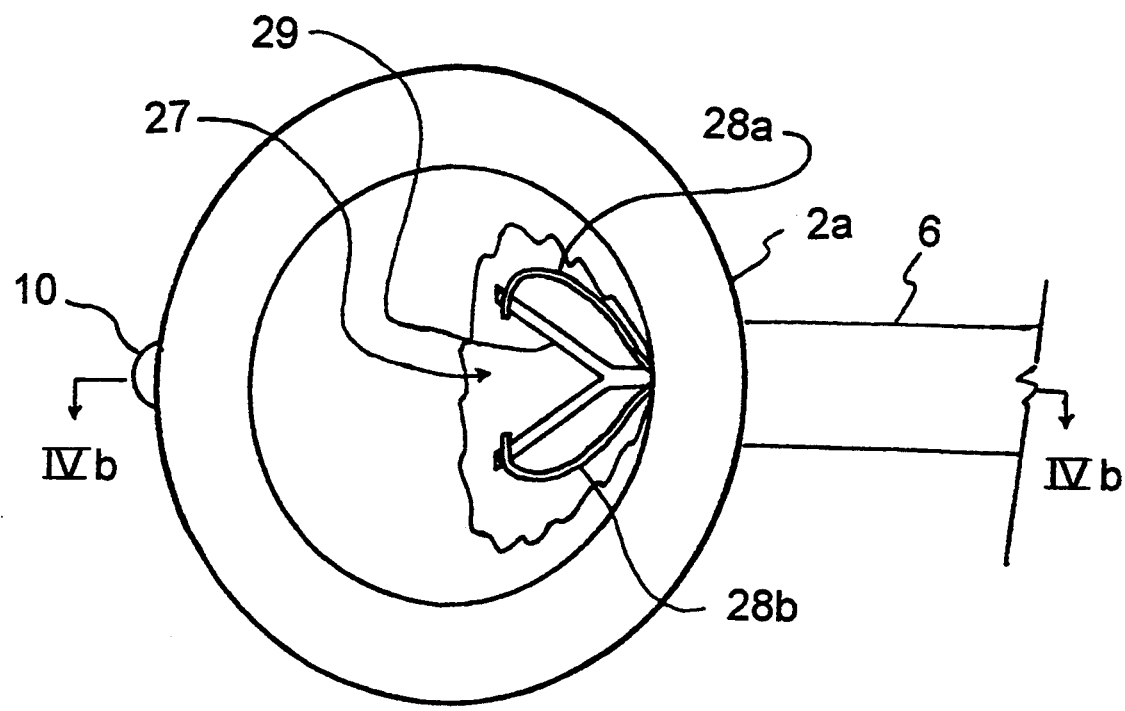
FIG. 4a shows a top plan cut-away view of still another embodiment of the present invention in a dip-type configuration employing an arrangement of fiber-optics to sense absorbance of the standard solution.
Figure 4B:
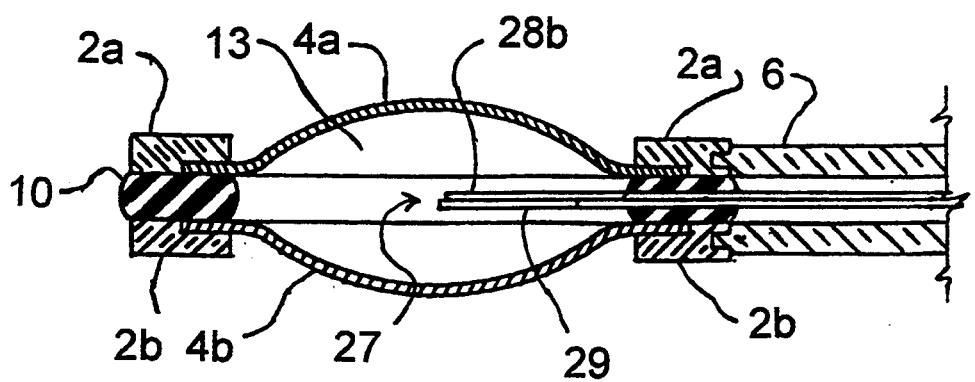
FIG. 4b shows a longitudinal cross-sectional view of the embodiment of FIG. 4a taken along line IVb—IVb.

Referring to FIGS. 4a and 4b, another embodiment of the present invention provides a dip-type sensor 20 similar to the above embodiment of FIGS. 3a and 3b except that the optical sensor 22 is replaced by a fiber-optic sensor 27. The cavity 13 once again has a standard solution (not shown) with a chromophore introduced therein. Optical fibers, 28a and 28b, extend into the cavity 13 and are support upon a yoke 29. Light, generated by an external source, is piped into the cavity via one of the optical fibers, 28a and 28b, and is sense and measured externally via another of the optical fibers, 28a and 28b.

Other embodiments of the present invention may employ a device for directly measuring a volume change of the chamber. Optical devices may measure an expansion of the chamber by monitoring incremental occlusion of light. Alternatively, mechanical devices may be employ that sense displacement of walls of the chamber. Other variations sensors of the present invention may be realized by those skilled in the art having viewed this disclosure which are within the scope and spirit of the present invention In both the above embodiments the membranes, 4a and 4b, are comprised of materials including flexible porous hydrophobic membrane materials. Various types of such materials, discussed below, are exceptionally suitable for the practice of the present invention. For example, porous polytetrafluoroethylene, sold under the trademark "GORETEX" and manufactured by W.L. Gore & Associates Inc., Elkton, Md. 21921, does not allow for the passage of water but is freely permeable to water vapor.

Another such membrane material is known by the trademark "SILON", manufactured by BioMed Sciences, Bethlehem, Pa. 18014, and is comprised of an interpenetrating network of two immiscible non-polar plastics, polydimethylsiloxane and polytetrafluoroethylene. These plastics do not adhere to one another or form an alloy. One plastic merely abuts against the other but does not fuse; therefore, there is a potential space between the two plastics and the interpenetrating network contains actual and potential minute canaliculi which connects one side of the membrane to the other.

A third porus film that is equally satisfactory for use in the present invention is a spun polyolefin film made by sintering polyolefin yarn. The interstices between fibers are too tiny to permit the passage of water yet permit the passage of gases and water vapor. This type of film is available under the trademark name "TYVEK", and is manufactured by DuPont Corporation.

As noted above, such membranes are not permeable to aqueous liquids because of the high surface tension of water droplets, however, gasses and water vapor readily pass from one side to the other. It is realized that other membranes in conjunction with water and other solvents provided that a similar vapor pressure relationship exists. Those skilled in the art, in view of the above disclosure, will recognize that other materials may be employed in the practice of the invention. Embodiments employing such materials are considered to be within the scope and spirit of the present invention.

Figure 5:
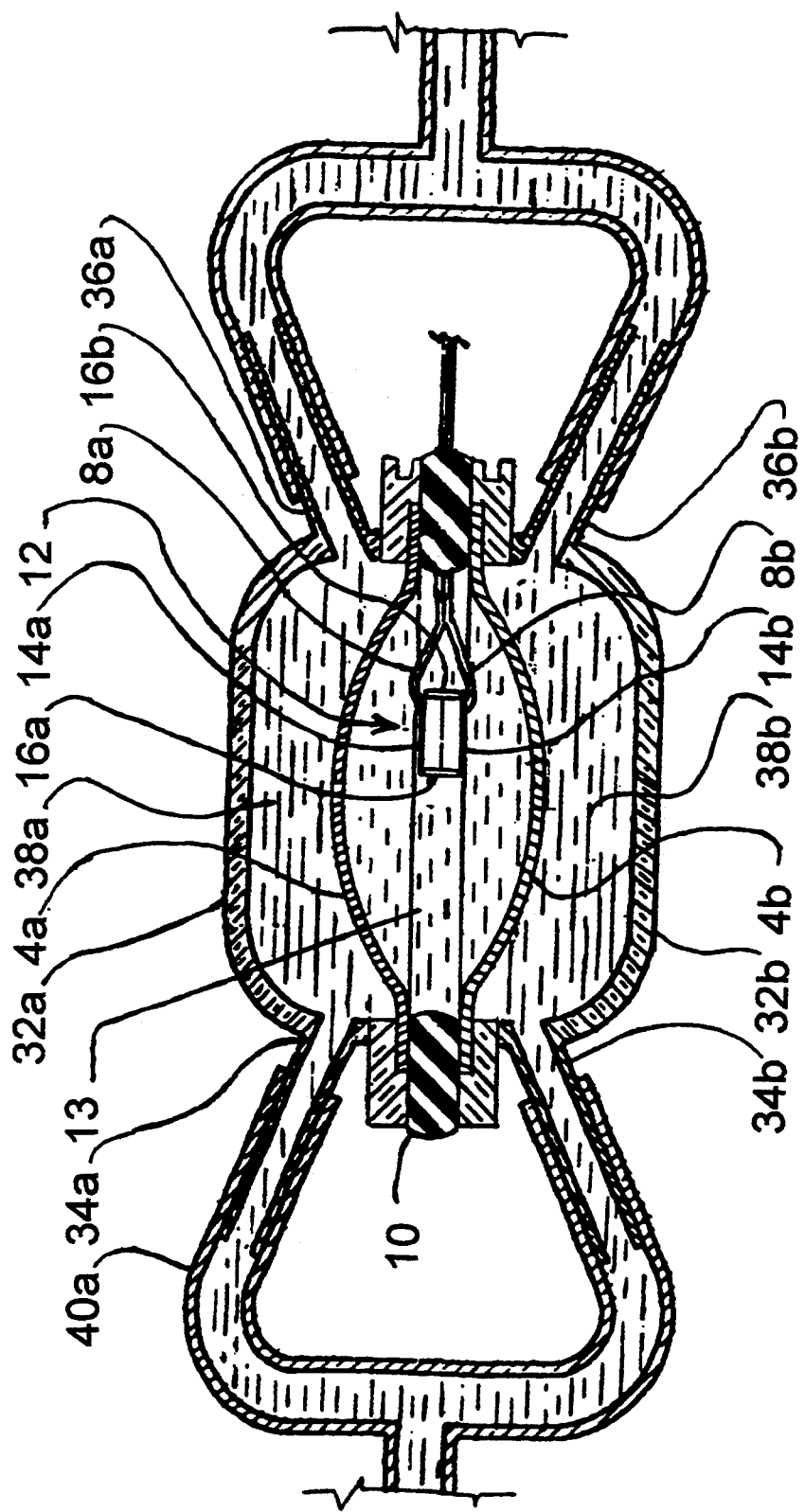
FIG. 5 shows a longitudinal cross-sectional view of an embodiment of the invention in a flow-through sensor configuration.

Referring to FIG. 5, another embodiment of the present invention is shown comprising a flow-through osmolarity sensor 30. The flow-through osmolarity sensor 30 is similar to the above embodiments except as stated below. A sealed outer shell includes first and a second concaved discs, 32a and 32b, which are fused together and take the place of the rings, 2a and 2b, of the dip-type sensor of FIG. 1. The first and second discs, 32a and 32b, are composed of a rigid plastic material such as polyolefin plastic. Tubular inlet ports, 34a and 34b, and tubular outlet ports 36a and 36b, are at opposing ends of concaved discs, 32a and 32b, respectively.

The tubular inlet ports, 34a and 34b, serve to introduce a specimen solution under test into first and second cavities, 38a and 38b, defined by the first concaved disc 32a and the first membrane 4a, and the second concaved disc 32b and the second membrane 4b, respectively. First and second tubular outlet ports, 36a and 36b, similarly release the specimen solution. A branched input splitter 40a accepts the specimen solution and distributes it to both the first and second cavities, 38a and 38b. The branched input splitter 40a ensures that the specimen solution in both the first and the second cavities, 38a and 38b, are of the same osmolarity. A branched output combiner 40b consolidates the specimen solution exiting the flow-through sensor 30.

The user charges the cavity 13 with the standard solution through the nipple 10 using a needle as described above with respect to the dip-type sensor 1 of FIG. 1. The sensor leads, 16a and 16b, are similarly connected to resistance measuring equipment (not shown) so that the conductance of the standard solution may be continuously monitored as the specimen solution continuously flows through the flow-through sensor 30. Thus, the flow through sensor permits continuous measurement of the osmolarity of the specimen solution.

In view of this disclosure, it would be clear to one skilled in the art that alternative embodiments of the present invention may be utilized. Numerous mechanical configurations exist wherein the standard solution may be separated from the specimen solution by a vapor-permeable membrane, possessing the properties described above, and wherein the specimen solution is permitted to flow around a membrane enclosure. For instance, a sac or a tube formed of membrane material may be suspended in a flow through housing containing a specimen solution. These and other embodiments, realizable in view of this disclosure, are within the scope and spirit of the present invention.

The above described embodiments of the present invention have many advantages including providing a means and a method for determining an osmolarity of a specimen solution without a need for expensive laboratory equipment and skilled technicians. Furthermore, the embodiments allow a real-time measurement of osmolarity to be made so that courses of action may be effectuated accordingly, eliminating the delay associated with laboratory measurements and allowing effective courses of action to be taken without a delay introduced by conventional means of measurement. Also among the advantageous of the present invention is a reduction in costs associated with the performance of such measurements and the effects of the delay associated with conventional techniques. Such delays are of critical importance where osmolarity measurements are required in order to determine a status of a patient under medical treatment, such as where kidney function is of interest as discussed above. The timely determination of osmolarity of urine allows treatment to be undertaken before significant damage results and allows the response to the treatment to be similarly monitored so that alternative treatments may be employed if necessary. While specific reference is made to the measurement of osmolarity of urine, it is understood that the present invention is not limited to such applications and may be employed generally where osmolarity of a solution is of interest.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An osmolarity sensor for measuring an osmolarity of a specimen solution, comprising:
   means for containing a standard solution including an aqueous solution of electrolytes;
   said means for containing defining a cavity, which is variable in volume, wherein the standard solution is held;
   said means for containing including a vapor-permeable membrane separating the standard solution from the specimen solution;
   said vapor-permeable membrane permitting passage of water vapor of the specimen solution and the standard solution, and blocking passage of solutes of said specimen solution; and
   means for sensing one of a conductivity and an absorbance of the standard solution, independent of positioning of said means for containing, and means, responsive to said means for sensing, for determining the osmolarity of the specimen solution when the standard solution has achieved substantial osmotic equilibrium with the specimen solution.

2. The osmolarity sensor of claim 1 wherein said vapor-permeable membrane blocks passage of water in its liquid phase.

3. The osmolarity sensor of claim 1 wherein said membrane includes a spun polyolefin film.

4. The osmolarity sensor of claim 1 wherein said membrane includes a microporous polytetrafluoroethylene.

5. The osmolarity sensor of claim 1 wherein said membrane includes a first immiscible non-polar plastic forming an interpenetrating network with a second immiscible non-polar plastic.

6. The osmolarity sensor of claim 1 wherein said membrane includes a polyolefin containing canalicular holes impervious to a passage of liquid water and permeable to a passage of water vapor wherein said solvent is liquid water.

7. The osmolarity sensor of claim 1 wherein said standard solution is effective for determining osmolarity where said specimen solution is urine.

8. The osmolarity sensor of claim 1 further comprising:
   a flow-through housing defining a chamber;

said means for containing said standard solution being disposed within said chamber;

inlet means for introducing said specimen solution into said chamber; and outlet means for releasing said specimen solution from said chamber so that said osmolarity of said specimen solution, flowing through said chamber, is continuously determined.

9. The osmolarity sensor of claim 1 further comprising a self-sealing nipple for introducing said standard solution into said cavity.

10. The osmolarity sensor of claim 1 wherein said means for sensing includes a conductance sensor for measuring a conductance of said standard solution so that a concentration and a volume thereof is determinable.

11. The osmolarity sensor of claim 1 wherein said means for sensing includes an optical sensor for measuring an absorbance of said standard solution due to a chromophore therein so that a concentration and a volume of said standard solution is determinable.

12. The osmolarity sensor of claim 1 wherein said means for containing includes the first semipermeable membrane and a second semipermeable arranged opposing said first semipermeable membrane for containing said standard solution therebetween and maximizing a surface area of semipermeable membrane exposed to said standard solution.

13. An osmolarity sensor for measuring an osmolarity of a specimen solution, comprising:

means for containing a standard solution including an aqueous solution of electorlytes;

said means for containing defining a cavity wherein the standard solution is held;

said means for containing including a vapor-permeable membrane separating the standard solution from the specimen solution;

said vapor-permeable membrane permitting passage of water vapor of the specimen solution and the standard solution, and blocking passage of solutes of said specimen solution; and means for sensing one of a conductivity and an absorbance of the standard solution, independent of positioning of said means for containing, and means, responsive to said means for sensing, for determining the osmolarity of the specimen solution when the standard solution has achieved substantial osmotic equilibrium with the specimen solution.

14. The osmolarity sensor of claim 13 wherein said vapor-permeable membrane blocks passage of water in its liquid phase.

15. The osmolarity sensor of claim 14 wherein said membrane includes one of a microporous polytetrafluoroethlene, a spun polyolefin film, and a first immiscible non-polar plastic forming an interpenetrating network with a second immiscible non-polar plastic.

16. The osmolarity sensor of claim 15 wherein said means for sensing includes an optical sensor, for measuring an absorbance of said standard solution due to a chromophore, so that a concentration and a volume of said standard solution is determinable.

17. The osmolarity sensor of claim 16 further comprising:

a flow-through housing defining a chamber;

said means for containing said standard solution being disposed within said chamber;

inlet means for introducing said specimen solution into said chamber; and outlet means for releasing said specimen solution from said chamber so that said osmolarity of said specimen solution, flowing through said chamber, is continuously determined.

18. The osmolarity sensor of claim 13 wherein said means for sensing a concentration includes one of a conductance sensor, for measuring a conductance of said standard solution, and an optical sensor, for measuring an absorbance of said standard solution due to a chromophore, so that a concentration and said volume of said standard solution is determinable.

19. The osmolarity sensor of claim 18 further comprising:

a flow-through housing defining a chamber;

said means for containing said standard solution being disposed within said chamber;

inlet means for introducing said specimen solution into said chamber; and outlet means for releasing said specimen solution from said chamber so that said osmolarity of said specimen solution, flowing through said chamber, is continuously determined.

20. The osmolarity sensor of claim 14 wherein said means for sensing includes an optical sensor, for measuring an absorbance of said standard solution due to a chromophore, so that said concentration and a volume of said standard solution is determined.

21. The osmolarity sensor of claim 17 wherein said means for containing includes the first semipermeable membrane and a second semipermeable arranged opposing said first semipermeable membrane for containing said standard solution therebetween and maximizing a surface area of semipermeable membrane exposed to said standard solution.

22. The osmolarity sensor of claim 17 wherein said means for sensing a volume is disposed between said first and second semipermeable membranes.

23. An osmolarity sensor, for measuring an osmolarity of a specimen solution, comprising:

means for containing a standard solution;

said means for containing defining a cavity wherein the standard solution is held;

said means for containing including a semipermeable membrane separating the standard solution from the specimen solution;

said semipermeable membrane permitting passage of a solvent of the specimen solution and the standard solution and blocking passage of solutes of said specimen solution; and means for sensing one of a conductivity and an absorbance of the standard solution, independent of positioning of said means for containing, and means, responsive to said means for sensing, for determining the osmolarity of the specimen solution when the standard solution has achieved substantial osmotic equilibrium with the specimen solution.

24. The osmolarity sensor of claim 23 wherein said means for containing includes the first semipermeable membrane and a second semipermeable arranged opposing said first semipermeable membrane for containing said standard solution therebetween and maximizing a surface area of semipermeable membrane exposed to said standard solution.

25. The osmolarity sensor of claim 24 wherein said means for sensing is disposed between said first and second semipermeable membranes.

26. The osmolarity sensor of claim 12 wherein said means for sensing is disposed between said first and second semipermeable membranes.

* * * * *